(12) United States Patent
Pasquet et al.

(10) Patent No.: US 8,236,056 B2
(45) Date of Patent: Aug. 7, 2012

(54) INTERVERTEBRAL IMPLANT FOR THE LUMBROSACRAL ARTICULATION

(75) Inventors: Denis Pasquet, Quinsac (FR); Regis Le Couedic, Andresy (FR); Jacques Senegas, Merignac (FR); Christian Renaud, Arthes (FR)

(73) Assignee: Zimmer Spine, Bordeaux (FR)

( * ) Notice: Subject to any disclaimer, the term of this patent is extended or adjusted under 35 U.S.C. 154(b) by 312 days.

(21) Appl. No.: 12/749,115

(22) Filed: Mar. 29, 2010

(65) Prior Publication Data

US 2010/0185243 A1     Jul. 22, 2010

Related U.S. Application Data

(63) Continuation of application No. 10/568,307, filed as application No. PCT/FR2004/002160 on Aug. 19, 2004, now Pat. No. 7,704,281.

(30) Foreign Application Priority Data

Aug. 21, 2003  (FR) ..................................... 03 10063

(51) Int. Cl.
*A61F 2/44* (2006.01)
(52) U.S. Cl. ................... 623/17.11; 623/17.13; 606/246; 606/249
(58) Field of Classification Search .... 623/17.11–17.16; 606/246–249
See application file for complete search history.

(56) References Cited

U.S. PATENT DOCUMENTS

| 5,810,815 | A | 9/1998 | Morales |
| 5,836,948 | A | 11/1998 | Zucherman et al. |
| 6,626,944 | B1 | 9/2003 | Taylor |
| 2003/0028250 | A1 | 2/2003 | Reiley et al. |
| 2003/0040746 | A1 | 2/2003 | Mitchell et al. |
| 2007/0203491 | A1 | 8/2007 | Pasquet et al. |

FOREIGN PATENT DOCUMENTS

| EP | 1138268 A | 10/2001 |
| FR | 2714591 A | 7/1995 |
| FR | 2775183 A1 | 2/1998 |
| FR | 2799640 A | 4/2001 |
| FR | 2822051 A | 9/2002 |
| WO | 02/071960 A1 | 9/2002 |

*Primary Examiner* — Andrew Yang
(74) *Attorney, Agent, or Firm* — Seager Tufte & Wickhem LLC

(57) ABSTRACT

The invention provides an intervertebral implant for the lumbo-sacral joint, the implant consisting in a spacer suitable for being placed between the fifth lumbar vertebra and the sacral vertebra articulated thereto, the body of said spacer presenting in its top face a groove extending in the midplane of the spacer and suitable for receiving the spinous process of said lumbar vertebra. A longitudinal housing oriented orthogonally to said groove is formed in the bottom face and is suitable for receiving the top portion of the sacral vertebra. The longitudinal housing is defined by an extension and by a tab of width narrower than the width of the body of the spacer. The section of the housing in the midplane of the space is generally U-shaped, being inclined relative to the bottom of the groove.

14 Claims, 3 Drawing Sheets

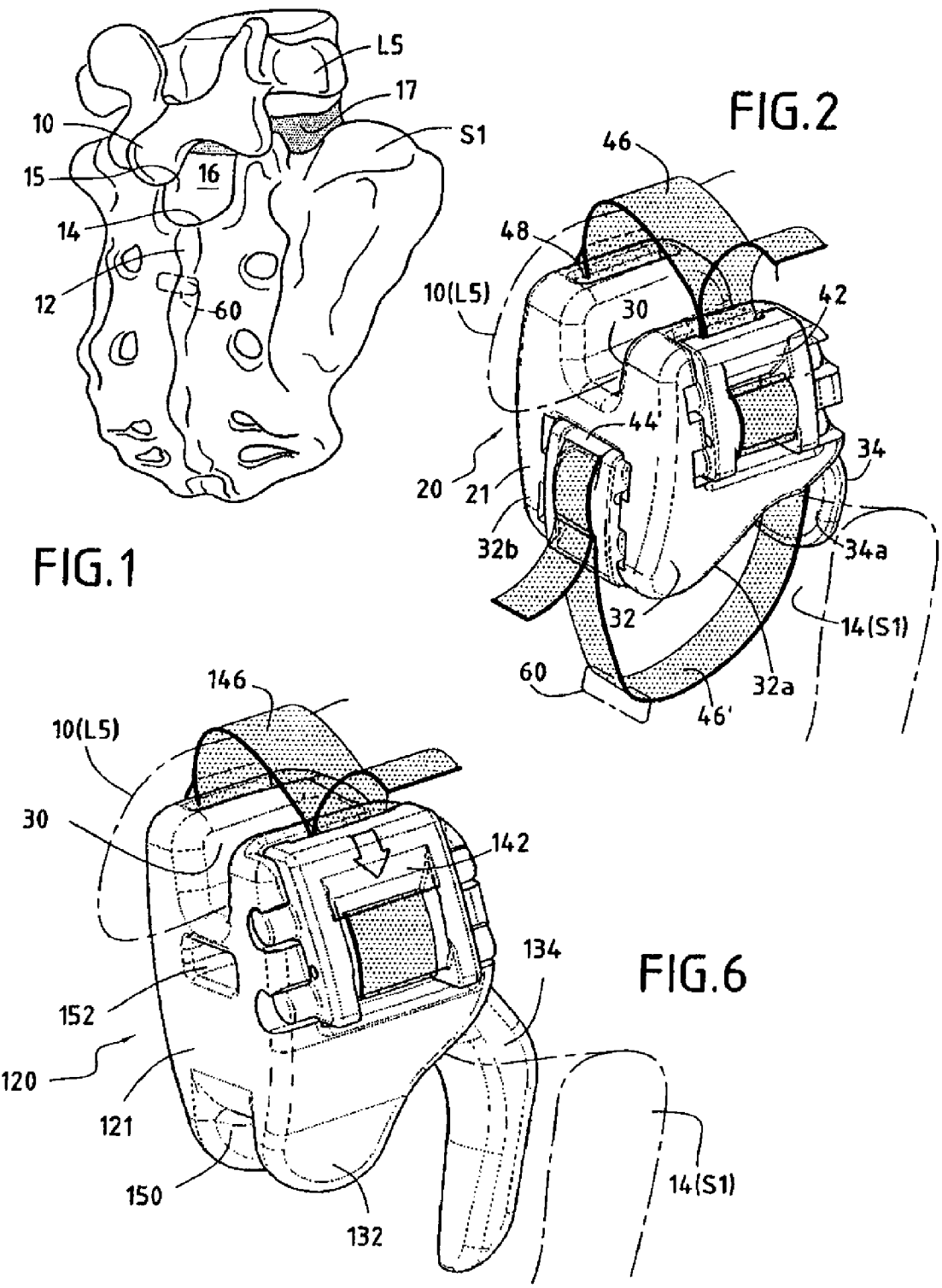

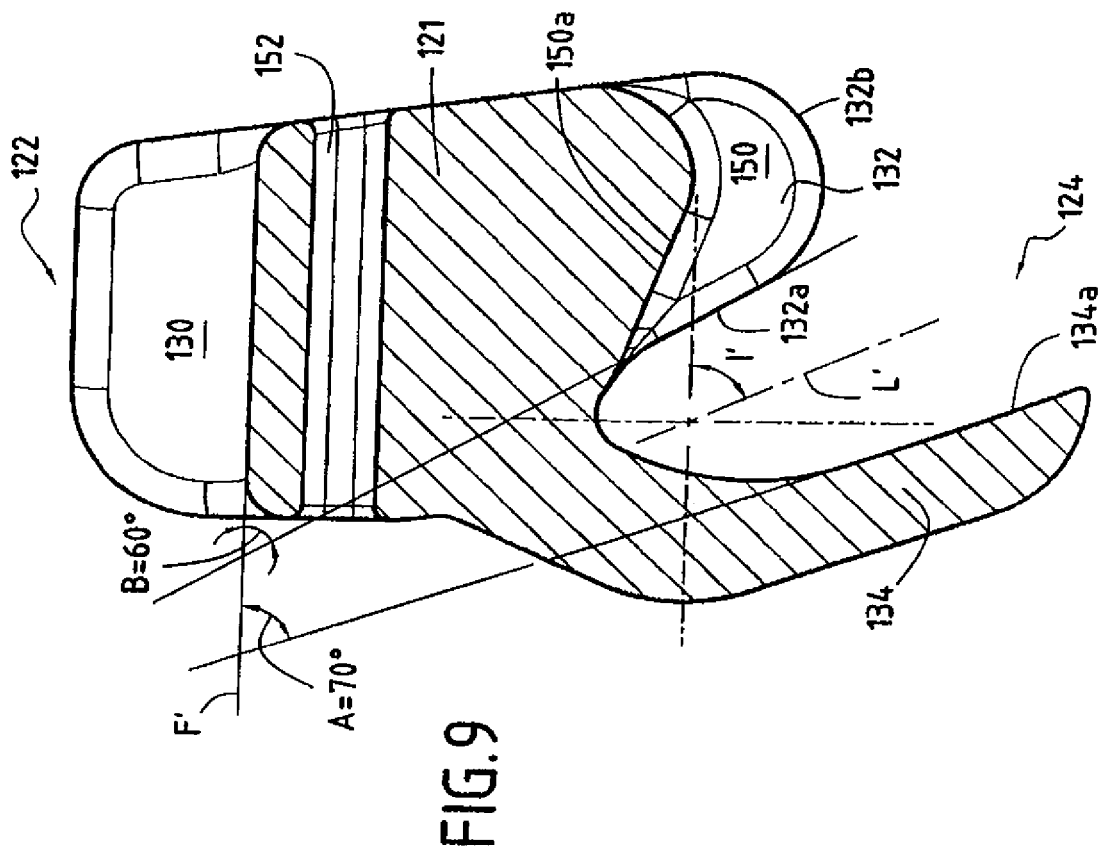
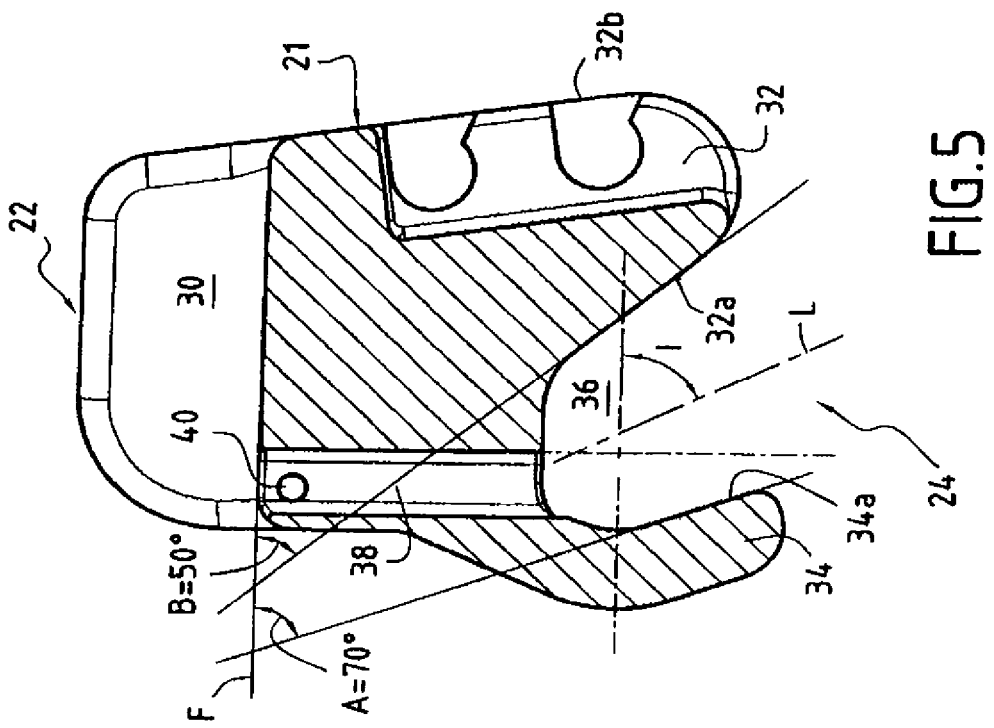

INTERVERTEBRAL IMPLANT FOR THE LUMBROSACRAL ARTICULATION

CROSS-REFERENCE TO RELATED APPLICATIONS

This application is a continuation of U.S. application Ser. No. 10/568,307, which is a 371 Application of PCT Patent Application No. PCT/FR04/02160, filed Aug. 19, 2004, which claims priority to French Application No. 0310063, filed Aug. 21, 2003, which are herein incorporated by reference in their entirety.

TECHNICAL FIELD

The present invention relates to an intervertebral implant for the lumbo-sacral joint.

BACKGROUND

In the anatomy of the spine, the sacrum, situated beneath the lumbar vertebrae, is constituted by five vertebrae which, over the course of human evolution, have become fused together. The top vertebra of the sacrum, written S1, is articulated to the fifth lumbar vertebra, written L5. This articulated connection constitutes the lumbo-sacral joint, or the L5-S1 joint, and is shown in FIG. 1.

Each lumbar vertebra presents a middle and posterior projection: the spinous process, sometimes referred to below as the process 10. The sacral vertebrae have lost their spinous processes during evolution, and instead they retain a small residual bulge 12.

In man, certain kinds of back pain can be due to stresses associated with relative movements between two vertebrae acting on the intervertebral disk situated between those vertebrae.

Numerous intervertebral implants are already known that seek to limit the movements of two vertebrae relative to each other so as to relieve the intervertebral disk, and in particular the implant described in document FR 2 775 183. That implant is a spacer presenting two longitudinal notches on its top and bottom faces extending in the same direction, that of the midplane of the spacer, for the purpose of receiving the spinous processes of the adjacent vertebrae between which the spacer is to be implanted. The spacer is then held in position by straps surrounding said processes. By blocking a portion of the spine, the spacer transfers loads from above and below the vertebrae concerned, thereby relieving the intervertebral disk situated between these vertebrae. Unfortunately, because of the anatomy of the sacral region, and more particularly because of the lack of a spinous process on vertebra S1, it is not possible to put that type of spacer into place over the L5-S1 joint.

A type of implant described in document EP 1 13 8 2 68 is also known that is specifically adapted for the anatomy of the lumbo-sacral region. That implant comprises an intervertebral spacer and a link bar. The intervertebral spacer presents two notches that are substantially mutually orthogonal, and the link bar is secured to the sacrum by means of two hooks secured to the vertebra S1. More precisely, the hooks bear against the top portion of the vertebra S1, also known as the posterior arc, and each of them is secured to the sacrum by fastener means such as staples that enable the hooks to be put into position and stabilized. Once the hooks are installed on the sacrum, the bar is secured to the hooks and the intervertebral spacer is put into place. The top notch in the spacer is suitable for receiving the spinous process on vertebra L5, while the bottom notch is of a shape that is suitable for receiving the bar, such that the spacer rests on the bar.

Nevertheless, that type of implant suffers from numerous drawbacks. Firstly, in the short term, fastening hooks to the sacrum, e.g. by staples, can be traumatic for the patient. Subsequently, in the medium to long term, the compression and extension stresses to which the implant is subjected are transferred to the means for fastening the hooks to the sacrum and lead to the holes in which the fastener means are secured becoming larger. Play is then created between the sacrum and the hooks, which can lead to the implant having poor mechanical behavior, or even to the fastener means being torn loose. The trauma suffered by the patient is then major, and a new operation must be envisaged in order to withdraw and possibly replace the defective implant.

The present invention seeks to solve the drawbacks of existing devices.

SUMMARY

To this end, the invention provides an intervertebral implant for the lumbo-sacral joint, the implant consisting of a spacer suitable for being placed between the fifth lumbar vertebra L5 and the vertebra S1 of the sacrum that is articulated thereto. The body of said spacer presents two opposite end faces, a top face and a bottom face. The spacer presents a groove extending along the midplane of the spacer and formed in the top end face and suitable for receiving the spinous process of said lumbar vertebra L5. The spacer also presents a longitudinal housing extending orthogonally to said groove and formed in the bottom end face, being suitable for receiving the top portion of the sacral vertebra S1, such that the spacer rests directly on said top portion.

The implant thus comprises no more than an intervertebral spacer, and the spacer can be put into direct contact with the sacral vertebra S1 without it being necessary to use other elements such as a fastener bar, thus making it easier to put into place.

In a first aspect of the invention, the body of said spacer presents first and second opposite side faces into which said groove opens out, and presents at its bottom end an extension having a first side extending the first side face, and a second side that is opposite from its first side and that defines a setback relative to the second side face of the body of the spacer, the spacer also including a tab of width narrower than the width of the body of the spacer in the direction orthogonal to the midplane of the spacer, connected to the body of the spacer, and extending facing the second side of said extension in such a manner that the inside face of said tab facing the second side of the extension co-operates with said second side to define the outline of said housing.

The small width of the tab enables the implant to adapt better to the anatomy of the sacral region. The top portion of the sacral vertebra S1 forms a posterior arc. This posterior arc is concave and co-operates with the anterior portion of the sacrum, known as the vertebral body, to define an orifice through which the spinal cord passes: the vertebral foramen. The invention seeks to limit the space occupied by the tab inside said orifice so as to leave as much space as possible available for the spinal cord, and thus avoid subjecting it to stresses that generally lead to pain for the patient.

For this purpose, the width of the tab is sufficiently narrow relative to that of the body of the spacer to enable it to engage deeply in the cavity formed by the posterior arc. Nevertheless, the dimensions of the tab cannot be made so small as to run the risk of it breaking under the effect of the stresses to which it is subjected. The width selected should therefore take account of the mechanical properties of the material used for making said tab.

It should be observed that the surface of the body of the spacer situated at the bottom of the housing, i.e. at the base of the tab, constitutes the surface whereby the spacer bears against the top edge of the posterior arc of the sacrum, and that the body of the spacer at this level must therefore be of a width that is sufficient to provide stable support.

Advantageously, the inside face of said tab situated facing the setback can be convex in such a manner as to present a shape that is complementary to the shape of the inside face of the posterior arc, facing towards the vertebral body. This characteristic enables the tab to fit closely to the shape of this wall and thus to occupy a limited amount of space inside the vertebral foramen.

According to a second aspect of the invention, the section in the midplane of the spacer of the housing formed in the bottom end face and suitable for receiving the top portion of vertebra S1, is generally U-shaped, and the midplane of this housing is not orthogonal to the midplane defined by the bottom of said groove.

The particular inclination and shape of the housing seek to improve the support of the spacer on the posterior arc of vertebra S1, which is not orthogonal to the portion of the spinous process of vertebra L5 that is to come into contact with the bottom of the groove, and having a top edge that presents a convex shape. These characteristics also make it easier to put the space into place.

Advantageously, the midplane of said housing is inclined relative to the midplane defined by the bottom of said groove at an angle lying in the range 40° to 80°. This inclination guarantees that the spacer is stable when it is in place.

Since the outline of the housing is defined by the inside face of the tab and the second side of said extension, the midplane of the housing extends relative to the midplane defined by the bottom of the groove in a manner that depends on the general inclination of the inside face of the tab and of the second side of the extension.

Thus, advantageously, a zone of the inside face of the tab slopes relative to the midplane defined by the bottom of said groove at an angle A lying in the range 60° to 80°, and preferably substantially equal to 70°, and a portion of the second side of the extension is inclined relative to the midplane defined by the bottom of said groove at an angle B lying in the range 40° to 70°, and preferably in the range 50° to 60°.

In another particular embodiment of the invention, a notch is formed in said extension facing said tab. The bulge situated on the posterior face of the sacrum, constituting the residual trace of a spinous process being present on sacral vertebra S1, is thus received within said notch when the implant is put into place, thus enabling the stability of the implant to be improved.

BRIEF DESCRIPTION OF THE DRAWINGS

The invention and its advantages can be better understood on reading the following detailed description of two embodiments of the invention shown in the accompanying figures.

FIG. 1 is a diagram showing the anatomy of the lumbo-sacral region of the spine.

FIG. 2 shows a first embodiment of the implant of the invention put into place between lumbar vertebra L5 and sacral vertebra S1.

FIG. 5 is a section view of the body of the FIG. 2 spacer on its midplane M.

FIG. 6 shows a second embodiment of the implant of the invention, put into place between lumbar vertebra L5 and sacral vertebra S1.

FIG. 9 is a section view of the body of the FIG. 6 spacer on its midplane M'.

DETAILED DESCRIPTION

Figure 3:
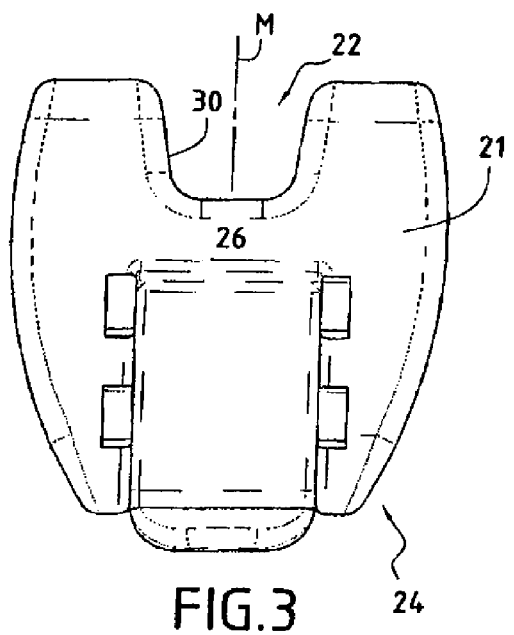
FIGS. 3 and 4 show said first and second side faces of the body of the FIG. 2 spacer.

The fifth lumbar vertebra L.5 and the top sacral vertebra S1 are shown diagrammatically in FIG. 1. In its middle posterior portion, vertebra L5 presents a spinous process 10. This process 10 is situated in the sagittal plane of the spine. The vertebra S1 does not possess a spinous process, and instead on its posterior face it presents a residual bulge 12.

The top portion of the vertebra S1 forms a posterior arc 14. The inside face of the posterior arc faces the vertebral body 15 of the sacrum, it is concave, and it co-operates with the vertebral body to define an orifice through which there passes the spinal cord (not shown), which orifice is known as the vertebral foramen 16.

As shown in FIGS. 2 and 6, the implant of the invention is suitable for being put into place between the spinous process 10 and the posterior arc 14. It makes it possible to limit the movement of the vertebra L5 relative to the vertebra S1 and thus enables the intervertebral disk 17 situated between these two 5 vertebrae to be relieved of the stresses that result from such movement.

With reference to FIGS. 2 to 5, there follows a description of a first embodiment of the intervertebral implant of the invention.

Figure 4:
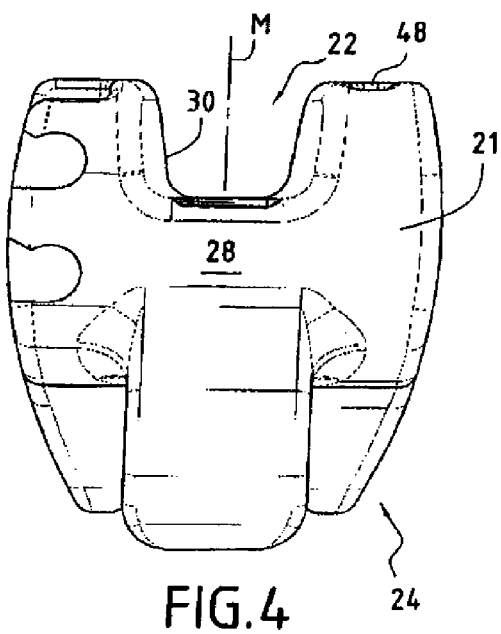

This implant consists in a spacer 20 whose body 21 is shown in FIGS. 3 to 5. The body of the spacer is made of a biocompatible material, e.g. a biopolymer. In the embodiment shown, the body 21 is molded out of polyetheretherketone, referred to below as PEEK. The polymer is of the type sold in particular under the trademark PEEK®.

The body 21 of the spacer presents a top end face 22 and a bottom end face 24 opposite from the face 22. It also presents first and second opposite side faces 26 and 28.

The midplane M of the spacer intersects the faces 22, 24, 26, and 28, and it subdivides the body 21 into two almost symmetrical portions that differ from each other only by the presence in one of the portions of a cavity that is suitable for receiving fastener means. When the spacer is put into place on the spine, the plane M corresponds substantially to the sagittal plane of the spine.

A groove 30 occupying the midplane M of the spacer 20 is formed in the top end face 22 of the body 21 and is suitable for receiving the process 10 of the lumbar vertebra L5. This groove opens out into the side faces 26 and 28. The section of the groove 30 in the plane perpendicular to the midplane M of the spacer is substantially U-shaped with a substantially plane base. This shape enables it to receive the bottom portion of the process 10.

The body 21 of the spacer 20 presents an extension 32 at its bottom end, which extension has a first side 32b extending the first side face 26, and a second side 32a opposite from the first side defining a setback relative to the second side face 28 of the body 21 of the spacer. The spacer 20 also comprises a tab 34 connected to the body 21 of the spacer, and in the present example integrally molded therewith. The tab 34 extends facing the second side 32a of the extension 32 and it is curved:

it begins by going away from the side 32a and from the face 26, prior to coming closer to the side 32a.

The size of the tab 34 in the direction orthogonal to the midplane M of the spacer 20, i.e. the width of the tab, is less than the width of the body 21 of the spacer. For example, the width of the tab 34 is substantially equal to 9 millimeters (mm), whereas the width of the body 21, and more particularly in the vicinity of the tab 34 in the zone that is to bear against the posterior arc 14 of the sacrum, is substantially equal to 18 mm, i.e. twice the width of the tab. The mean thickness of the tab 34 is substantially equal to 2 mm. For a tab 34 made of PEEK, these dimensions are sufficient to enable the tab 34 to withstand the stresses to which it is subjected.

The inside face 34a of the tab 34 facing towards the second side 32a of the extension, co-operate with said second side to define the outside of a longitudinal housing 36. This housing 36 formed in the bottom end face 24 extends orthogonally relative to the groove 30 and is suitable for receiving the posterior arc 14 of the sacral vertebra S1. Thus, once put into place, the spacer 20 rests directly on the sacrum.

In order to facilitate contact between the spacer 20 and the posterior arc 14 of the sacrum, the section of the housing 36 in the midplane M of the spacer is generally U-shaped, and the midplane L of the housing 36 is not orthogonal to the midplane F defined by the bottom of the groove 30.

More precisely, in the example shown, the midplane L of the housing 36 is inclined relative to the midplane F at an angle I lying in the range 50° to 70°. This inclination depends firstly on the general inclination of the inside face 34a of the tab 34 relative to the plane F, and secondly on the inclination of the second side 32a of the extension 32 relative to said plane. Thus, a zone of the inside face 34a of the tab 34 is inclined relative to the midplane F at an angle A that is substantially equal to 70° as shown in FIG. 5, and a portion of the second side 32a of the extension 32 is inclined relative to the midplane F at an angle B that is substantially equal to 50°.

As shown in FIG. 1, the spacer also presents first and second fastener means 42 and 44 serving to enable the body 21 of the spacer to be secured respectively to the process 10 of the lumbar vertebra L5, and to the sacral vertebra S1.

These fastener means are similar to those described in document FR 01/03362, each comprising a strap 46, 46' and a fastener system secured to the body of the spacer.

The fastener system is formed by a plate suitable for being received inside a cavity of complementary shape formed in the body 21 of the spacer. The plate presents studs on two of its opposite side edges suitable for being engaged by force into housings provided for this purpose in the cavity of the body 21 so as to be held therein. This enables the plate to be secured to the body 21 of the spacer.

Each plate also presents two slots through which the straps 46, 46' can be passed. These slots are inclined so as to allow the straps to move in one direction only, corresponding to tightening.

Concerning the first fastener means 42, the first end on the strap 46 is passed through an oblong opening 48 situated along a first side of the groove 30 and passing through the body 21 of the spacer, and is then folded over and stitched to itself so as to form a loop. The first end of the strap 46 is thus secured to the body of the spacer 21.

The other end of the strap 46 is passed into a fastener system situated along the side of the groove 30 that is opposite from said first side. When the spacer is put into place, the strap 46 is tightened around the process 10.

The second fastener means 44, different from the first, are shown in FIGS. 2 and 5. As can be seen in FIG. 5, a hole 38 is formed in the body 21 of the spacer and opens out on one side into the bottom of the housing 36 in the vicinity of the tabs 34, and on the other side into the bottom of the groove 30. This hole is suitable for receiving a portion of the strap 46'. In the vicinity of the groove 30, another hole 40 is formed in the body 21. This hole 40 crosses the hole 38 orthogonally and is smaller in diameter than the hole 38. The hole 40 opens out on one side of the body of the spacer and is suitable for receiving a pin (not shown).

The strap 46' is slid into the hole 38 and the pin is passed into a loop formed at the first end of said strap 46'. Thus, the first end of the strap 46' is secured to the body 21 of the spacer by means of the pin. The other end 46' is passed into the fastener system 44 situated on the first side face 26 of the body of the spacer.

As shown in FIG. 2, when the spacer is in place, the strap 46' passes between the posterior arch 14 of the sacrum and the inside face 34a of the tab 34, then along a portion of the vertebra S1, prior to passing through an opening 60 made for this purpose in the sacrum after which it rises back towards the fastener system 44.

When the body 21 of the spacer and the tab 34 are made of PEEK, and the strap 46' is made of woven polyester yarn, the outside face of the tab is smoother than the face of the strap. It is then advantageous since less trauma is involved for the spinal cord, to encourage contact between the tab 34 and the spinal cord and to limit contact between the strap 46' and the spinal cord. That is why the tab 34 covers the strap 46' when the spacer is in place.

A second embodiment of the implant of the invention is shown in FIGS. 6 to 10. This implant likewise consists in a spacer 120. Since the shape of this spacer is close to that of the first embodiment, the numerical references specifying the portions of the spacer 12 0 that are similar to portions of the spacer 20 correspond to the numerical references used for the spacer 20 plus 100.

The top portion of the body 121 of the spacer 120 is identical to that of the body 21 of the spacer 20; the body 121 presents a groove 130 for receiving the process of the vertebra L5, and the first fastener means 142 comprise a strap 146 held by a fastener system and serving to be tightened around the process 10 in such a manner as to hold it in the groove 130.

The bottom portion of the body 121 differs from that of the body 21. Firstly, the tab 134 is longer and wider than the tab 34. The tab 134 seeks to replace the fastener means 44 for fastening the spacer 20 to the sacrum, and therefore needs to be long enough to descend along the posterior arc 14 of the vertebra S1 and to ensure that the spacer 120 is held on said arc 14. Furthermore, since it is subjected to high levels of stress, its length and its thickness, mainly in the vicinity of the body 121 of the spacer must be sufficient to prevent any breakage. The thickness of the tab 134 is compensated by the absence of the strap, such that like the first embodiment, once the spacer 120 is in place, the tab 134 occupies as little space as possible inside the vertebral foramen, so as to limit contact with the spinal cord.

The housing 136 situated in the bottom end face 124 of the spacer is defined by the tab 134 and the extension 132. The section of this housing 136 on the midplane M of the spacer is generally U-shaped, and the mean plane L' of said housing is inclined relative to the mean plane F' defined by the bottom of the groove 130 by an angle I' lying in the range 60° to 70°. The angles A and B represent respectively the inclination between a zone of the inside face 134a of the tab 134 and the mean plane F' defined by the bottom of the groove 130, and the inclination between a portion of the second side 132a of the extension 132 and the mean plane F', and these angles are substantially equal respectively to 70° and 60°.

Since the spacer does not have any means for fastening it to the sacrum, the walls of the housing 136 are closer to each other than in the first embodiment, and the angle that exists between the second side 132a of the extension 132 and the inside face 134a of the tab 134 is substantially equal to 10°, whereas it is nearer 20° in the first embodiment. Thereafter, the bottom of the housing 136 presents a concave shape that is more marked in order to receive more closely the top edge of the vertebra S1 which is convex.

Figure 7:
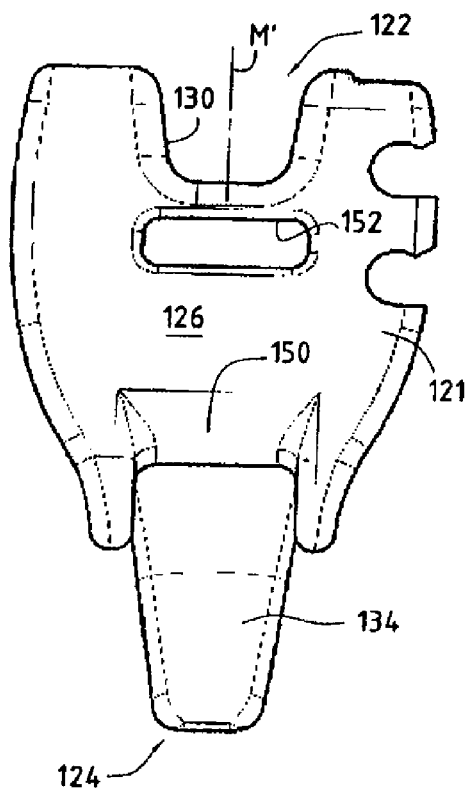
FIGS. 7 and 8 show said first and second side faces of the body of the FIG. 6 spacer.
Figure 8:
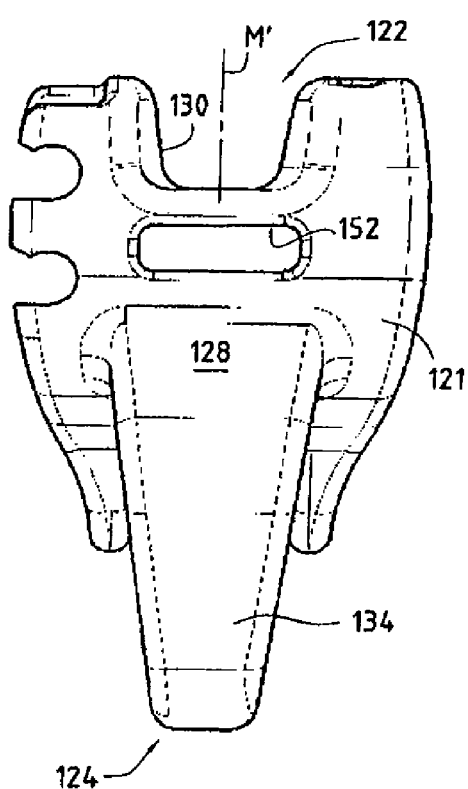

Furthermore, as shown in FIGS. 6, 7, and 9, a notch 150 is formed in the extension 132 facing the tab 134 so that when the spacer is being put into place, the residual bulge 12 situated on the posterior face of the vertebra S1 is received in the notch 150, thus improving the stability of the spacer 120 on the sacrum. The bottom 150a of the notch 150 may be substantially parallel to the mean plane $F^1$, or it may be inclined relative to said plane at an angle that is substantially equal to 20°, as shown in FIG. 9.

The spacer 120 also presents a hole 152 parallel to the plane F' defined by the bottom of the groove 130 and situated beneath said groove, passing through the body 121 of the spacer 120. This hole opens out into the first and second side faces 126 and 128 of the body of the spacer 120, and is provided to pass an instrument that is used for holding the spacer 120 while it is being put into place.

The invention claimed is:

1. A method of limiting the displacement of the fifth lumbar vertebra relative to the sacral vertebra of a spinal column, the fifth lumbar vertebra including a spinous process and the sacral vertebra including a vertebral foramen defined between a posterior arc of the sacral vertebra and a vertebral body of the sacral vertebra, the method comprising:
    inserting a spacer of an intervertebral implant between the fifth lumbar vertebra and the sacral vertebra such that the spinous process of the fifth lumbar vertebra is received in a groove of the spacer and rests directly against the spacer and the posterior arc of the sacral vertebra is received in a longitudinal housing of the spacer and rests directly against the spacer.

2. The method of claim 1, wherein the longitudinal housing is defined between a surface of an extension of the spacer and a surface of a tab spaced from the extension.

3. The method of claim 2, wherein the housing extends generally orthogonal to the groove.

4. The method of claim 2, wherein the tab of the spacer is inserted into the vertebral foramen of the sacral vertebra between the posterior arc of the sacral vertebra and the vertebral body of the sacral vertebra.

5. A method of limiting the displacement of the fifth lumbar vertebra relative to the sacral vertebra of a spinal column, the method comprising:
    providing an intervertebral implant comprising:
        a spacer having a superior end, an inferior end opposite the superior end, an anterior face, and a posterior face opposite the anterior face;
        the superior end of the spacer including a groove defined between a first side surface and a second side surface, wherein the groove is adapted to receive a spinous process of the fifth lumbar vertebra between the first side surface and the second side surface, the groove extending through the spacer from the anterior face to the posterior face;
        the inferior end of the spacer including an extension having a first side and a second side, and a tab spaced from the extension, wherein a housing extending generally orthogonal to the groove is defined between the second side of the extension and a side face of the tab facing the extension, wherein the housing is adapted to receive a top portion of the sacral vertebra between the second side of the extension and the side face of the tab; and
    inserting the intervertebral implant between the fifth lumbar vertebra and the sacral vertebra such that the spinous process of the fifth lumbar vertebra is received in the groove of the spacer and rests directly against the spacer and the top portion of the sacral vertebra is received in the longitudinal housing of the spacer and rests directly against the spacer.

6. The method of claim 5, wherein the tab of the spacer is inserted into a vertebral foramen of the sacral vertebra defined between a posterior arc of the sacral vertebra and a vertebral body of the sacral vertebra.

7. The method of claim 5, further comprising:
    securing the spinous process of the fifth vertebra in the groove by tightening a strap of the intervertebral implant against the spinous process.

8. The method of claim 5 further comprising:
    securing the top portion of the sacral vertebra in the housing by tightening a strap of the intervertebral implant against the sacral vertebra.

9. The method of claim 8, further comprising:
    forming an opening through the sacral vertebra; and
    passing the strap through the opening of the sacral vertebra.

10. The method of claim 5, wherein the spacer includes a midplane which intersects each of the superior end, the inferior end, the anterior face and the posterior face of the spacer, the midplane bisecting the groove.

11. The method of claim 10, wherein the tab has a width measured in a direction orthogonal to the midplane of the spacer which is less than a width of the extension measured in a direction orthogonal to the midplane of the spacer.

12. The method of claim 5, wherein a first portion of the tab curves away from the extension and a second portion of the tab curves toward the extension.

13. The method of claim 5, wherein the side face of the tab is convex.

14. The method of claim 5, wherein a notch formed in the extension receives a residual bulge on the sacral vertebra.

* * * * *